United States Patent [19]

Hajduch

[11] Patent Number: 4,955,864
[45] Date of Patent: Sep. 11, 1990

[54] TUBE HOLDING CLAMP

[76] Inventor: James D. Hajduch, 1703 Caroline Ave., Whiting, Ind. 46394

[21] Appl. No.: 416,876

[22] Filed: Oct. 4, 1989

Related U.S. Application Data

[63] Continuation-in-part of Ser. No. 637,019, Aug. 2, 1984, abandoned.

[51] Int. Cl.⁵ ............................................ A61M 39/00
[52] U.S. Cl. ..................... 604/174; 604/179; 606/151; 606/157; 128/DIG. 15; 128/DIG. 26
[58] Field of Search ............... 128/DIG. 15, DIG. 26; 604/174–179; 606/151, 157

[56] References Cited

U.S. PATENT DOCUMENTS

| | | | |
|---|---|---|---|
| 2,463,400 | 3/1949 | Lowe | 604/174 |
| 3,297,026 | 1/1967 | Van Pelt | 128/DIG. 15 |
| 3,722,508 | 3/1973 | Roberts | 128/DIG. 26 |
| 3,812,851 | 5/1974 | Rodriguez | 604/179 |
| 4,250,880 | 2/1981 | Gordon | 128/214 R |
| 4,480,639 | 11/1984 | Peterson et al. | 604/179 |
| 4,569,348 | 2/1986 | Hassinger | 604/179 |
| 4,591,356 | 5/1986 | Christie | 604/179 |

Primary Examiner—Benjamin Layno
Attorney, Agent, or Firm—Frank J. Uxa, Jr.

[57] ABSTRACT

An improved apparatus for holding tubing, e.g., intravenous tubing, comprises a clamp housing, and at least one tubing clip secured to the housing and being capable of being opened and closed to accept and hold, respectively, a segment of hollow tubing without changing the cross-sectional shape of the segment of hollow tubing. A method for holding a segment of hollow tubing is also disclosed.

20 Claims, 1 Drawing Sheet

TUBE HOLDING CLAMP

RELATED APPLICATION

This application is a continuation-in-part of application Ser. No. 637,019, filed Aug. 2, 1984 now abandoned.

BACKGROUND AND SUMMARY OF INVENTION

This invention relates to an apparatus and methods for holding a segment of hollow tubing, e.g., intravenous tubing. More particularly, the present invention relates to such apparatus and methods which have applicability in the medical and human health care industries. This invention may also be used by veterinarians.

The medical and health care industry is becoming more and more sophisticated. It is often necessary, in order to properly treat patients, to transport fluids, e.g., nutrients, blood, oxygen and the like, via hollow tubes to and from a patient. Intravenous feeding and medication is becoming common place. Kidney dialysis involves repeated transporting of blood from and back to a patient.

Often there are two or more separate lines or segments of hollow tubing being used to treat a single patient. Unless care is taken, these tubes can become tangled and, ultimately, restricted or closed to the passage of fluid.

Recent advances in needle technology have resulted in the use of flexible needles Such flexible needles are effective without requiring that the member, e.g., the patient's arm or leg, in which the needle is stuck be completely immobilized With prior rigid needles, such immobilization was necessary to prevent needle breakage and/or inadvertent removal from the member. Thus, flexible needles allow more patient movement and, therefore, comfort during treatment.

Many prior tubing clamps were structured to hold the tubing so tightly as to, in effect, immobilize the patient. That is, the prior tubing clamps often held the tubing so as to prevent substantially any movement of the tubing or the patient. Also, these prior tubing clamps, in holding the tubing tightly, often "squeezed down" on the tubing and caused an unwanted and unneeded constraint on the flow of fluid through the tubing.

A new apparatus and method useful for holding a segment of hollow tubing has been discovered. The present apparatus effectively holds the segment of hollow tubing so as to orient its longitudinal axis, as desired, e.g., to avoid tangling with other segments of hollow tubing. Importantly, however, the present apparatus does not constrict the hollow tubing and, therefore, does not increase the resistance to flow through the hollow tubing. In addition, the present system can provide for holding a segment of hollow tubing without immobilizing the tubing. This allows a medical patient to whom the segment of hollow tubing is attached, e.g., through a needle, to have substantial freedom of movement, thus making the patient's treatment more comfortable and easy to withstand. Further, the present apparatus is portable and adaptable to various applications, and is easy and relatively inexpensive to manufacture.

In one embodiment, the present apparatus comprises a clamp housing means and clip means secured to the clamp housing means, preferably removably secured to the clamp housing means. This clip means is sized and adapted to be opened to accept a segment of hollow tubing and to be closed around the segment of hollow tubing without changing the cross-sectional shape of the segment of hollow tubing. Preferably, this clip means is sized and adapted to be closed around the segment of hollow tubing substantially without frictionally contacting the segment of hollow tubing. In other words, the clip means preferably provides substantially no resistance to the axial movement of the segment of hollow tubing. The present clip means is preferably structured to be repeatedly opened and closed.

In a particularly useful embodiment, the present apparatus further comprises second clip means secured, preferably removably secured, to the clamp housing means and spaced apart from the clip means, described above. This second clip means is sized and adapted to be opened to accept a segment of hollow tubing and to be closed around the segment of hollow tubing without changing the cross-sectional shape of the segment of the hollow tubing. A sleeve is also provided and surrounds the segment of hollow tubing, and is preferably secured thereto. This sleeve is located between the two clip means when both of the clip means are closed around the same segment of hollow tubing. The sleeve is sized so as not to move from between the two closed clip means. In this manner, the segment of hollow tubing can be held in place by the two clip means without changing the cross-sectional shape of the hollow tubing, and preferably without frictionally contacting the hollow tubing.

The present apparatus preferably further comprises clamp holding means associated with the clamp housing means and adapted to secure, more preferably removably secure, the clamp housing means to a stationary object, in particular an object other than the medical patient being treated. In one embodiment, the clamp holding means includes a hook or loop segment secured to the clamp housing means and a securing means having a corresponding loop or hook segment capable of being secured to a stationary object, so that when the securing means is secured to the stationary object and the hook or loop segment and the corresponding loop or hook segment are fastened together, the clamp housing means is secured to the stationary object. The clamp apparatus may include an elongated strap means having a first surface of hooks and an opposing second surface of loops. The elongated strap means is capable of acting as the securing means or of being wrapped around a member, for example, an extremity of a human being, and at least one segment of tubing so that the first and second surfaces fasten together, thereby maintaining the tubing in contact with the member.

In another aspect of the present invention, a method for holding a segment of hollow tubing is provided. In one embodiment, this method comprises providing a clamp comprising a clamp housing means and clip means secured to the clamp housing means. This clip means is as described above. A segment of hollow tubing is placed in the clip means when the clip means is open. The opened clip means is closed around the segment of hollow tubing in the clip means and maintained around the segment of hollow tubing without changing the cross-sectional shape of the segment of hollow tubing.

In another embodiment, the present method for holding a segment of hollow tubing comprises providing a clamp comprising clamp housing means and spaced apart first and second clip means secured to the clamp housing means. Each of the first and second clamp means is sized and adapted in a manner similar to the clip means and second clip means, respectively, described above. A segment of hollow tubing is placed in each of the first and second clip means when the first and second clip means, respectively, is opened. A portion of the segment of hollow tubing is surrounded by, and preferably secured to, a sleeve having a larger cross-section than the segment of hollow tubing. This sleeve is located between the first and second clip means. The first and second clip means are closed around the segment of hollow tubing in the first and second clip means and maintained around the segment of hollow tubing and between the sleeve without changing the cross-sectional shape of the segment of hollow tubing.

Substantial advantages are obtained from the present invention. Among those advantages include preventing the tubing from becoming tangled and/or from becoming obstructed to fluid flow.

These and other aspects and advantages of the present invention are set forth in the following detailed description and claims, particularly when considered in conjunction with the accompanying drawings in which like parts bear like reference numerals.

DETAILED DESCRIPTION OF THE DRAWINGS

Figure 1:
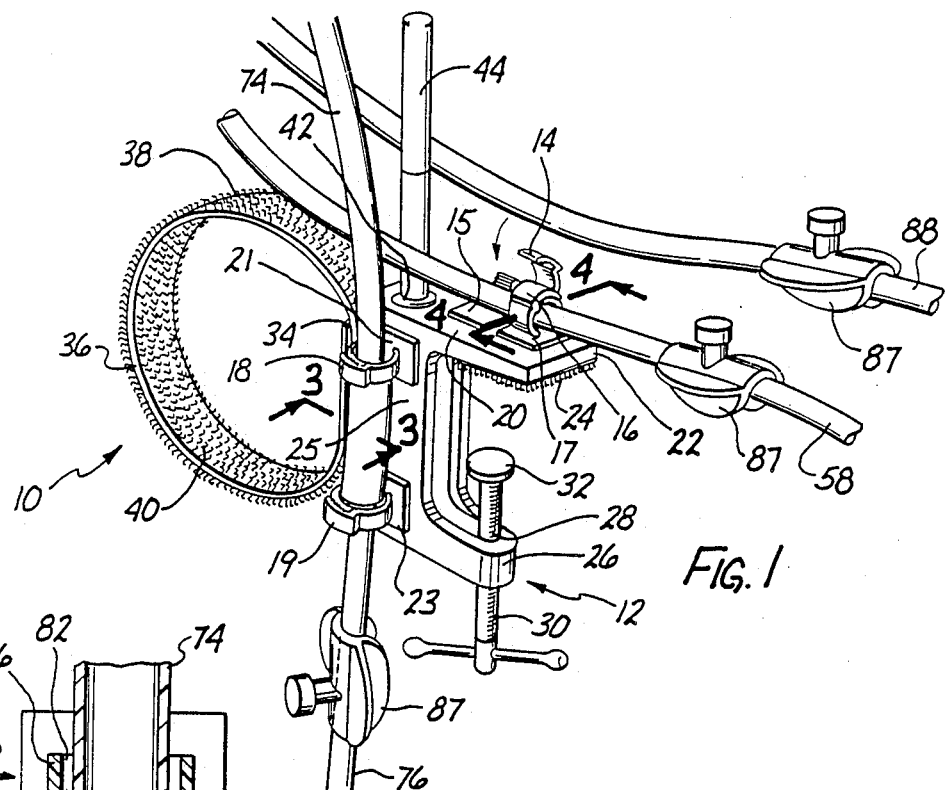
FIG. 1 is a side frontal view, in perspective, of a tube clamp embodiment of the present invention.

Referring now to the drawings, FIG. 1 shows a tube clamp, shown generally at 10, which includes clamp housing 12, horizontal tube clips 14 and 16, and vertical tube clips 18 and 19. Horizontal tube clips 14 and 16 include adhesive mats 15 and 17, respectively, and are removably secured to the top surface 20 of the upper wing 22 of clamp housing 12. Vertical clamp 18 and 19 include adhesive mats 21 and 23 respectively and are removably secured to the side surface 25 of clamp housing 12. These adhesive mats are conventional and allow tube clips 14, 16, 18 and 19 to be secured to clamp housing 12 or removed therefrom, as desired. Thus, each of the tubing clips 14, 16, 18 and 19 can be individually placed on clamp housing 12 in any one of a number of positions to satisfy the requirements of the application involved. Also, more or less tubing clips than the four (4) shown in the drawings may be provided to meet the requirements of the application involved. Extending downwardly from and secured to the lower surface of upper wing 22 is a first loop surface 24.

Extending through the lower wing 26 of clamp housing 12 is a threaded hole 28 which is adapted to receive threaded screw 30. Screw head 32 is affixed to the top of threaded screw 30.

A second loop surface 34 is adhesively secured to the side of clamp housing 12. It should be noted that tubing clamp 10 may include more than one loop surface 34 or loop surface 34 may be placed anywhere on clamp housing 12, as desired, to function, e.g., as described below. Also, any or all of the loop surfaces and the hook surfaces described herein may be changed to hook and loop surfaces, respectively, as desired, provided that when any two of these surfaces are brought together, as described herein, a hook-loop fastener combination is obtained.

Strap 36 includes an outer hook surface 38 and an inner loop surface 40. This inner loop surface 40 is shown in FIG. 1 as being an extension of second loop surface 34.

Clamp housing 12 has a hole 42 extending down from the top of clamp housing 12. Hole 42 is adapted to receive and hold a writing instrument, e.g., pen 44, for the use and convenience of the medical practitioner using tubing clamp 10.

Figure 2:
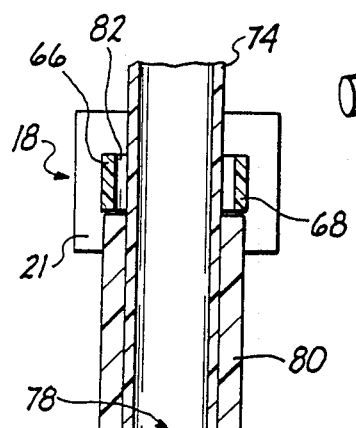
FIG. 2 is a side frontal view, in perspective, of a bed rail clamp suitable for use with the tube clamp shown in FIG. 1.

Referring to FIG. 2, bed rail clamp, shown generally at 46, includes a clamp hook surface 48 and two bed rail holders 50 and 52 which can be adapted to wrap around and become secured to a circular pole, such as a bed rail.

Figure 4:
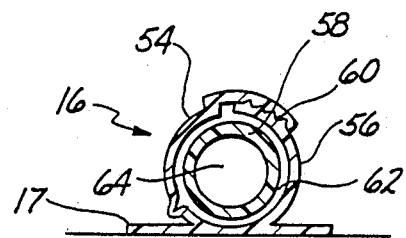
FIG. 4 is a cross-sectional view taken generally along line 4—4 of FIG. 1.

Referring now to FIG. 4, horizontal tube clip 16 includes adhesive mat 17, first clip element 54 and second clip element 56. Each of the other tube clips 14, 18 and 19 are structured and operated analogously to tube clip 16. To open tube clip 16, first clip element 54 is separated from second clip element 56 and moved to the left side, as shown in FIG. 4. With tube clip 16 opened, hollow tubing segment 58 is placed between first and second clip elements 54 and 56, which are then brought together to close tube clamp 16 around hollow tubing segment 58. A conventional snap-type mechanism 60 is provided to securely close tube clip 16. In this closed configuration, tube clip 16 forms a hollow space 62 which has a larger diameter than the outer diameter of hollow tubing segment 58. Thus, even with tube clip 16 closed around hollow tubing segment 58, tube clip 16 does not change or distort the cross-sectional shape of hollow tubing element 58, nor does it come into frictional contact with hollow tubing segment 58. In this manner, tubing clip 16 controls the axial orientation of hollow tubing segment 58, but does not restrict the flow of fluid through hollow space 64 of hollow tubing segment 58, nor does it restrict the axial movement of hollow tubing segment 58. Thus, the patient to whom hollow tubing segment 58 is attached to is able to move quite freely about while undergoing treatment, thus making the treatment more comfortable, or at least more bearable.

Figure 3:
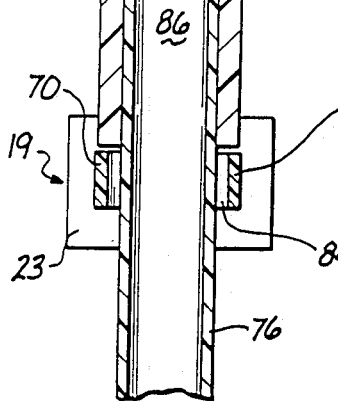
FIG. 3 is a cross-sectional view taken generally along line 3—3 of FIG. 1.

Referring now to FIG. 3, vertical tube clips 18 and 19 are shown. Tube clip 18 includes adhesive mat 21, first clip element 66 and second clip element 68. Tube clip 19 includes adhesive map 23, first clip element 70 and second clip element 72. Two similarly structured lengths of hollow tubing 74 and 76 are abutted together at region 78. A sleeve 80 surrounds first and second lengths of hollow tubing 74 and 76 and acts to adhesively hold first and second lengths of tubing 74 and 76 together at region 78. Sleeve 80 is located between tube clips 18 and 19 and has a cross-sectional area so that when tube clips 18 and 19 are closed, sleeve 80 can not pass through either of the spaces 82 or 84 formed by tube clip 18 and 19, respectively. In this manner, first and second lengths of hollow tubing 74 and 76 are "locked" in place without the tube clips 18 and 19 distorting the cross-sectional shape of or restricting the flow of fluid through the hollow space 86 formed by the lengths of hollow tubing 74 and 76.

Conventional flow restrictors 87 are secured to the hollow tubing to control the flow of fluid through the hollow tubing. These flow restrictors can be set, as desired, without any interference, e.g., flow-restriction, caused by the presence of the tubing clip or clips.

Tubing clamp 10 functions as follows. First, tubing clamp 10 is secured in place. Ordinarily, this is accomplished by positioning tubing clamp 10 so that a stationary object other then the medical patient being treated is between first loop surface 24 and screw head 32. Threaded screw 30 is then turned until tubing clamp 10 is secured to the stationary object. If this is not possible, e.g., because the stationary object is irregularly shaped, strap 36 is wrapped around the stationary object and then fastened to second loop surface 34, thereby securing tubing clamp 10 to the stationary object. If it is desired to secure tubing clamp 10 to a bed rail (or other similar object), bed rail holders 50 and 52 are wrapped around and secured to the bed rail and clamp hook surface 48 is brought into contact with first loop surface 24 to form a hook-loop fastener and secure tubing clamp 10 to the bed rail.

In any event, once tubing clamp 10 is secured, it is ready for use. As shown in FIG. 1, it is desired to have tubes 58 and 88 both run horizontally. Therefore, tube clips 14 and 16 are suitably positioned on the top surface 20 of upper wing 24 of clamp housing 12. Tube clips 14 and 16 are then opened to receive hollow tubing segments 88 and 58, respectively, and then closed so as to loosely hold hollow tubing segments 88 and 58. Tubing lengths 74 and 76 are secured together with sleeve 80, e.g., using adhesive and/or other conventional techniques of securing a polymeric sleeve to polymeric tubing, and then placed in tube clips 18 and 19 so that sleeve 80 is located therebetween. This arrangement allows tubing clips 18 and 19 to effectively lock the tubing lengths 74 and 76 in place without interfering with the flow of fluid through these tubing lengths. Sleeve 80 is secured to tubing lengths 74 and 76 so that substantially no change in the cross-sectional shape of the tubing lengths 74 and 76 occurs. Thus, the sleeve 80 provides substantially no additional resistance to the flow of fluid through the tubing lengths 74 and 76.

In the event strap 36 is not used to secure tube clamp 10 in place, it may be wrapped around the area of the patient, e.g., the patient's arm, where the tube or tubes enter the body to hold the tube or tubes in place. When strap 26 is wrapped around any area of the patient, it may also be wrapped around at least one segment of hollow tubing, e.g., to maintain the tubing in contact with the patient. Thus strap 36 may be used in place of tape for patients who are allergic to tape. In addition, strap 36 may be used in this manner repeatedly whereas tape is costly and can only be used once.

While this invention has been described with respect to various specific examples and embodiments, it is to be understood that the invention is not limited thereto and that is can be variously practiced within the scope of the following claims.

What is claimed is:

1. An apparatus useful for holding a segment of hollow tubing comprising: clamp housing means; and clip means secured to said clamp housing means, said clip means being sized and adapted to be opened to accept a segment of hollow tubing and to be closed around the segment of hollow tubing without substantially changing the cross-sectional shape of the segment of hollow tubing and substantially without frictionally contacting the segment of hollow tubing.

2. The apparatus of claim 1 wherein said clip means is structured to be repeatedly opened and closed.

3. The apparatus of claim 1 wherein said clip means is removably secured to said clamp housing means.

4. The apparatus of claim 1 which further comprises clamp holding means associated with said clamp housing means and adapted to secure said clamp housing means to a stationary object.

5. The apparatus of claim 4 wherein said apparatus is for use in treating a medical patient and said clamp holding means is adapted to secure said clamp housing means to a stationary object other than the medical patient being treated.

6. The apparatus of claim 4 wherein said clamp holding means includes a hook or loop segment secured to said clamp housing means and a securing means having a corresponding loop or hook segment adapted to be associated with a stationary object, so that when said securing means is secured to said stationary object, and said hook or loop segment and said corresponding loop or hook segment are fastened together, said clamp housing means is secured to said stationary object.

7. The apparatus of claim 1 which further comprises second clip means secured to said clamp housing means and spaced apart from said clip means, said second clip means being sized and adapted to be opened to accept a segment of hollow tubing and to be closed around the segment of hollow tubing without changing the cross-sectional shape of the segment of the hollow tubing; and sleeve means surrounding the segment of hollow tubing and located between said clip means and said second clip means when both said clip means and said second clip means are closed around the same segment of hollow tubing, said sleeve means being sized so as not to move from between said closed clip means and said closed second clip means.

8. The apparatus of claim 7 wherein said clip means and said second clip means are independently removably secured to said clamp housing means.

9. A method for holding a segment of hollow tubing comprising:
providing a clamp comprising clamp housing means and clip means secured to said clamp housing means, said clip means being sized and adapted to be opened to accept a segment of hollow tubing and to be closed around the accepted segment of hollow tubing:
placing a segment of hollow tubing in said clip means when said clip means is opened,
closing said opened clip means around said segment of hollow tubing in said clip means; and
maintaining said closed clip means around said segment of hollow tubing without substantially changing the cross-sectional shape of said segment of hollow tubing and substantially without frictionally contacting said segment of hollow tubing.

10. The method of claim 9 wherein said segment of hollow tubing is used in the treatment of a medical patient.

11. A method for holding a segment of hollow tubing comprising:
providing a clamp comprising clamp housing means and spaced apart, first and second clip means secured to said clamp housing means, each of said first and second clip means being sized and adapted to be opened to accept a segment of hollow tubing and to be closed around the accepted segment of hollow tubing;

placing a segment of hollow tubing in each of said first and second clip means when said first and second clip means, respectively, is opened, provided that a portion of said segment of hollow tubing is surrounded by a sleeve having a larger cross-section than said segment of hollow tubing, and said sleeve is located between said first and second clip means;

closing each of said opened first and second clip means around said segment of hollow tubing in said first and second clip means, respectively; and maintaining said closed first and second clip means around said segment of hollow tubing and between said sleeve without changing the cross-sectional shape of said segment of hollow tubing.

12. The method of claim 11 wherein said closed first and second clip means are maintained around said segment of hollow tubing substantially without frictionally contacting said segment of hollow tubing.

13. The method of claim 11 wherein said sleeve acts further to couple together two separate lengths of hollow tubing.

14. The method of claim 11 wherein said segment of hollow tubing maintained between said closed first and second clip means is used in the treatment of a medical patient.

15. An apparatus useful for holding a segment of hollow tubing comprising: clamp housing means; first clip means secured to said clamp means, said first clip means being sized and adapted to be opened to accept a segment of hollow tubing and to be closed around the segment of hollow tubing substantially without changing the cross-sectional shape of the segment of hollow tubing;

second clip means secured to said clamp housing means and spaced apart from said first clip means, said second clip means being sized and adapted to be opened to accept a segment of hollow tubing and to be closed around the segment of hollow tubing substantially without changing the cross-sectional shape of the segment of the hollow tubing; and sleeve means surrounding the segment of hollow tubing and located between said first clip means and said second clip means when both said first clip means and said second clip means are closed around the same segment of hollow tubing, said sleeve means being sized so as not to move from between said closed first clip means and said closed second clip means.

16. The apparatus of claim 15 wherein said first clip means and said second clip means are independently removably secured to said clamp housing means.

17. The apparatus of claim 15 wherein said sleeve means acts further to couple together two separate lengths of hollow tubing.

18. The apparatus of claim 15 wherein each of said first clip means and said second clip means is sized and adapted to be closed around the segment of hollow tubing substantially without frictionally contacting the segment of hollow tubing.

19. The apparatus of claim 15 wherein each of said first clip means and said second clip means is structured to be repeatedly opened and closed.

20. The apparatus of claim 15 which further comprises clamp holding means associated with said clamp housing means and adapted to secure said clamp housing means to a stationary object.

* * * * *